United States Patent
Blondin et al.

(10) Patent No.: US 9,551,000 B2
(45) Date of Patent: Jan. 24, 2017

(54) METHOD FOR CONTROLLING THE PRODUCTION OF SULPHITES, OF HYDROGEN SULPHIDE AND OF ACETALDEHYDE BY YEASTS

(71) Applicants: INSTITUT NATIONAL DE LA RECHERCHE AGRONOMIQUE, Paris (FR); CENTRE INTERNATIONAL D'ETUDES SUPERIEURES EN SCIENCES AGRONOMIQUES (MONTPELLIER SUPAGRO), Montpellier (FR)

(72) Inventors: Bruno Blondin, Montpellier (FR); Jessica Noble, Montpellier (FR); Isabelle Sanchez, Montpellier (FR)

(73) Assignees: INSTITUTE NATIONAL DE LA RECHERCHE AGRONOMIQUE, Paris (FR); CENTRE INTERNATIONAL D'ETUDES SUPERIEURES EN SCIENCES AGRONOMIQUES (MONTPELLIER SUPAGRO), Montpellier (FR)

( * ) Notice: Subject to any disclaimer, the term of this patent is extended or adjusted under 35 U.S.C. 154(b) by 0 days.

(21) Appl. No.: 14/374,475

(22) PCT Filed: Jan. 24, 2013

(86) PCT No.: PCT/IB2013/050623
§ 371 (c)(1),
(2) Date: Jul. 24, 2014

(87) PCT Pub. No.: WO2013/111091
PCT Pub. Date: Aug. 1, 2013

(65) Prior Publication Data
US 2014/0335524 A1 Nov. 13, 2014

(30) Foreign Application Priority Data

Jan. 25, 2012 (FR) ..................... 12 50717

(51) Int. Cl.
| | | |
|---|---|---|
| C12N 1/00 | (2006.01) |
| C12Q 1/68 | (2006.01) |
| C12N 15/00 | (2006.01) |
| C12N 15/74 | (2006.01) |
| C12N 15/81 | (2006.01) |
| C07K 14/395 | (2006.01) |
| C12N 9/10 | (2006.01) |
| C12P 3/00 | (2006.01) |
| C12P 7/24 | (2006.01) |
| C12N 15/10 | (2006.01) |
| C12N 15/70 | (2006.01) |
| C12N 1/18 | (2006.01) |

(52) U.S. Cl.
CPC ............ *C12N 15/81* (2013.01); *C07K 14/395* (2013.01); *C12N 9/1029* (2013.01); *C12P 3/00* (2013.01); *C12P 7/24* (2013.01); *C12Q 1/6895* (2013.01); *C12Y 203/01031* (2013.01); *C12G 2200/11* (2013.01); *C12N 1/18* (2013.01); *C12N 15/102* (2013.01); *C12N 15/70* (2013.01); *C12Q 1/6883* (2013.01); *C12Q 2600/156* (2013.01); *Y02P 20/52* (2015.11)

(58) Field of Classification Search
CPC ......... C12N 1/18; C12N 15/81; C12N 15/102; C12N 15/70; C12Q 1/6883
See application file for complete search history.

(56) References Cited

U.S. PATENT DOCUMENTS

| | | |
|---|---|---|
| 2010/0143536 A1 | 6/2010 | Bisson et al. |
| 2012/0071542 A1 | 3/2012 | Zhu et al. |

FOREIGN PATENT DOCUMENTS

| | | |
|---|---|---|
| WO | WO 2008/115759 | 9/2008 |
| WO | WO 2009/030863 | 3/2009 |
| WO | WO 2009/046485 | 4/2009 |

OTHER PUBLICATIONS

Bowie et al. (Science, 1990, 257:1306-1310).*
Yoshida et al. (Oct. 2010) "A novel mechanism regulates H$_2$S and SO$_2$ production in *Saccharomyces cerevisiae*," *Yeast*. 28:109-21.
Hansen et al. (1996) "Inactivation of MET2 in brewer's yeast increases the level of sulfite in beer," *J. Biotechnol*. 50:75-87.
Kim et al. (2009) "Dissecting the pleiotropic consequences of a quantitative trait nucleotide," *FEMS Yeast Research*. 9(5):713-722.
Berlese-Noble et al. (Aug. 28, 2012) "A new and powerful strategy to control SO$_2$ and H$_2$S production by wine yeasts," ICY2012. Poster Session Food and Beverage (Area H)—Abstract Only.
Cordente et al. (2009) "Isolation of sulfite reductase variants of a commercial wine yeast with significantly reduced hydrogen sulfide production," *FEMS Yeast Res*. 9:446-459.
Linderholm et al. (2010) "Identification of MET10-932 and characterization as an allele reducing hydrogen sulfide formation in wine strains of *Saccharomyces cerevisiae*," *Appl. Environ. Microbiol*. 76:7699-7707.
Marullo et al. (2007) "Efficient use of DNA molecular markers to construct industrial yeast strains," *FEMS Yeast Res*. 7:1295-1306.

(Continued)

*Primary Examiner* — Gary Nickol
*Assistant Examiner* — Lakia Tongue
(74) *Attorney, Agent, or Firm* — Lathrop & Gage LLP

(57) ABSTRACT

The present invention relates to the identification of alleles of the MET2 and SKP2 genes having the effect of reducing the production of sulphites, of hydrogen sulphide and of acetaldehyde by *Saccharomyces*, and to the use of these alleles in methods for controlling the production of these compounds during alcoholic fermentation.

4 Claims, 3 Drawing Sheets

(56) References Cited

OTHER PUBLICATIONS

International Search Report with Written Opinion corresponding to International Patent Application No. PCT/IB2013/050623, mailed Jan. 10, 2013.
International Preliminary Report on Patentability corresponding to International Patent Application No. PCT/IB2013/050623, issued Jul. 29, 2014.

* cited by examiner

METHOD FOR CONTROLLING THE PRODUCTION OF SULPHITES, OF HYDROGEN SULPHIDE AND OF ACETALDEHYDE BY YEASTS

CROSS-REFERENCE TO RELATED APPLICATIONS

This application is a U.S. National Stage Application under 35 U.S.C. §371 of International Application No. PCT/IB2013/050623, filed Jan. 24, 2013, which claims the benefit of and priority to French Patent Application No. 1250717, filed Jan. 25, 2012. Each of these applications is hereby incorporated by reference in its entirety.

BACKGROUND

The present invention relates to the control of the production of sulfites, of hydrogen sulfide and of acetaldehyde during alcoholic fermentation by yeasts.

Sulfur dioxide ($SO_2$) and its various forms in equilibrium in solution ($HSO_3^-$, $SO_3^-$), collectively denoted sulfites, are used as additives in enology, principally to improve the conservation of wines, owing to its antioxidant and antibacterial properties. However, an excessive amount of sulfites in wine can lead to intolerances and allergies in certain consumers; they may also be prejudicial to its organoleptic qualities, given that they give, if there in excess, drying sensations. Excessive amounts of sulfites at the end of alcoholic fermentation can thus be disadvantageous when the wine producer wants to carry out malolactic fermentation. Lactic acid bacteria, responsible for this fermentation, are inhibited by low sulfite contents, and an excess delays the initiation of said fermentation. Hydrogen sulfide is also a metabolite formed by yeasts in fermentation which is prejudicial to the quality of wines when it is present in excess owing to the "rotten egg" or "reduced" tastes that it imparts.

It is therefore important to be able to optimize the amount of sulfites and of hydrogen sulfide in wines and during winemaking. A major difficulty in this context comes from the fact that part of the sulfites and of the hydrogen sulfide present in the wine come from the fermentative metabolism of yeasts, where they constitute intermediates in the synthesis of sulfur-containing amino acids. Inorganic sulfate enters the cell by means of a sulfate permease. It is activated to give adenosylphosphosulfate (APS) by ATP-sulfurylase, then the APS is phosphorylated by adenosylphosphosulfate kinase to produce phosphoadenosylphosphosulfate (PAPS). The PAPS is then reduced to $SO_2$ by PAPS reductase. The $SO_2$ is reduced to $H_2S$ by sulfite reductase. Homocysteine, which is the precursor of sulfur-containing amino acids, is synthesized by reaction of $H_2S$ with O-acetylhomoserine, catalyzed by O-acetylhomoserine sulfhydrylase.

Since the amount of sulfites produced by yeasts during fermentation varies from one yeast strain to another, this complicates the control of the overall sulfite content. The same is true for hydrogen sulfide, the amount of which formed depends greatly on the yeast strain.

Another compound, the presence of which in wine above certain amounts is considered to be undesirable, is acetaldehyde. Acetaldehyde at too high a concentration gives wines "musty" notes which are considered to be negative. It is produced by yeasts during fermentation, and its production appears to correlate with the $SO_2$ content, and like that of the $SO_2$, varies from one yeast strain to another.

Various approaches have been proposed for obtaining yeast strains producing reduced amounts of sulfites and/or of hydrogen sulfide.

PCT application WO 2008/115759 and PCT application WO 2009/046485, and also the publications by Cordente et al. (FEMS Yeast Res, 9, 446-59, 2009) and Linderholm et al. (Appl Environ Microbiol, 76, 7699-707, 2010), describe various mutations in the MET5 or MET10 genes (encoding the 2 catalytic subunits of sulfite reductase) which have the effect of reducing hydrogen sulfide production. Application WO 2009/030863 and the publication by Marullo et al. (FEMS Yeast Res, 7, 1295-306, 2007) describe various markers associated with characteristics of interest in enological yeasts. One of these markers (YOL083w) located on chromosome XV is associated with a reduced $H_2S$ production.

SUMMARY

The inventors have now identified alleles of two genes involved in sulfur metabolism in Saccharomyces, as being associated with a reduced production of $SO_2$, of acetaldehyde and, in the case of one of these genes, of $H_2S$.

The first of these genes is the SKP2 gene, located on chromosome XIV (nt 49397 to 51688 in the Saccharomyces genome database). The corresponding cDNA sequence and the corresponding polypeptide sequence (for the reference Saccharomyces cerevisiae S288C strain) are available in the GenBank database under the respective accession numbers NM_001183149.1 (GI:296147470) and NP_014088.1 (GI: 6324018). SKP2 encodes a protein of F-box type which is involved in the stability of various sulfur metabolism proteins and in particular of adenosylphosphosulfate kinase responsible for the conversion of APS to PAPS. It has recently been shown (Yoshida et al., Yeast, 28, 109-21, 2011) that the inactivation of the SKP2 gene results in a stabilization of adenosylphosphosulfate kinase, and in an increase in the production of $H_2S$ and of $SO_2$.

The inventors have identified, in the SKP2 gene, two mononucleotide polymorphisms which differentiate the JN10 strain from the JN17 strain: one in position 50 618 of chromosome XIV, where the JN10 strain has a G and the JN17 strain has an A, and the other in position 50 640 bp where the JN10 strain has a C, whereas the JN17 strain has a T. These polymorphisms are reflected by the changing of a valine for JN10, to isoleucine for JN17, at position 350 of the Skp2 protein (V350I), and also of a threonine in JN10 at position 357 of Skp2, to isoleucine in JN17 (T357I).

The SKP2 gene allele present in the JN17 strain had not been previously identified in any other strain of Saccharomyces. The cDNA sequence of this allele is indicated in the appended sequence listing under the number SEQ ID NO: 1, and the deduced polypeptide sequence under the number SEQ ID NO: 2.

The second gene is the MET2 gene, also located on chromosome XIV (nt 117349 to 118809, coordinates indicated in the Saccharomyces genome database (http:www.yeastgenome.org) on Dec. 27, 2011). The corresponding cDNA sequence and the corresponding polypeptide sequence (for the reference Saccharomyces cerevisiae strain S288C) are available in the GenBank database under the respective accession numbers NM_001183115.1 (GI: 296147504) and NP_014122.1 (GI:6324052). MET2 encodes homoserine-O-acetyl transferase which catalyzes the conversion of homoserine to O-acetyl homoserine, which is then condensed with $H_2S$ to form homocysteine. It has been shown (Hansen & Kielland-Brandt, J Biotechnol, 50, 75-87, 1996) that the inactivation of the MET2 gene in *Saccharomyces* leads to an increase in the production of sulfites and of hydrogen sulfide.

The inventors have identified, in position 118 249 of chromosome XIV, a mononucleotide polymorphism which differentiates the MET2 genes of two *Saccharomyces cerevisiae* strains, one (JN10 strain) a strong producer of $SO_2$, $H_2S$ and acetaldehyde under certain fermentation conditions, and the other (JN17 strain) a weak producer of these same compounds. The JN10 strain has a C whereas the JN17 strain has (like the reference strain S288C) a G, which leads to an amino acid change and the conversion of an arginine in the JN10 strain to glycine in the JN17 strain in position 301 of the Met2 protein (R301G).

A subject of the present invention is a method for obtaining a yeast strain of the *Saccharomyces* genus producing a lower amount of $SO_2$, hydrogen sulfide and acetaldehyde than that produced by the parent strain from which it is derived, said method being characterized in that it comprises:

the selection of a parent strain containing an allele of the SKP2 gene, hereinafter known as $SKP2^{(350/357)X}$, encoding an Skp2 protein in which the amino acid in position 350 and/or the amino acid in position 357 is (are) other than an isoleucine or isoleucines, and/or an allele of the MET2 gene, hereinafter known as $MET2^{301X}$, encoding a Met2 protein in which the amino acid in position 301 is other than a glycine;

the introduction, into said parent strain, of an allele of the SKP2 gene, hereinafter known as $SKP2^{(350/357)I}$, encoding an Skp2 protein in which the amino acid in position 350 and/or the amino acid in position 357 is (are) an isoleucine or isoleucines, and/or of an allele of the MET2 gene, hereinafter known as $MET2^{301G}$, encoding a Met2 protein in which the amino acid in position 301 is a glycine.

Figure 1:
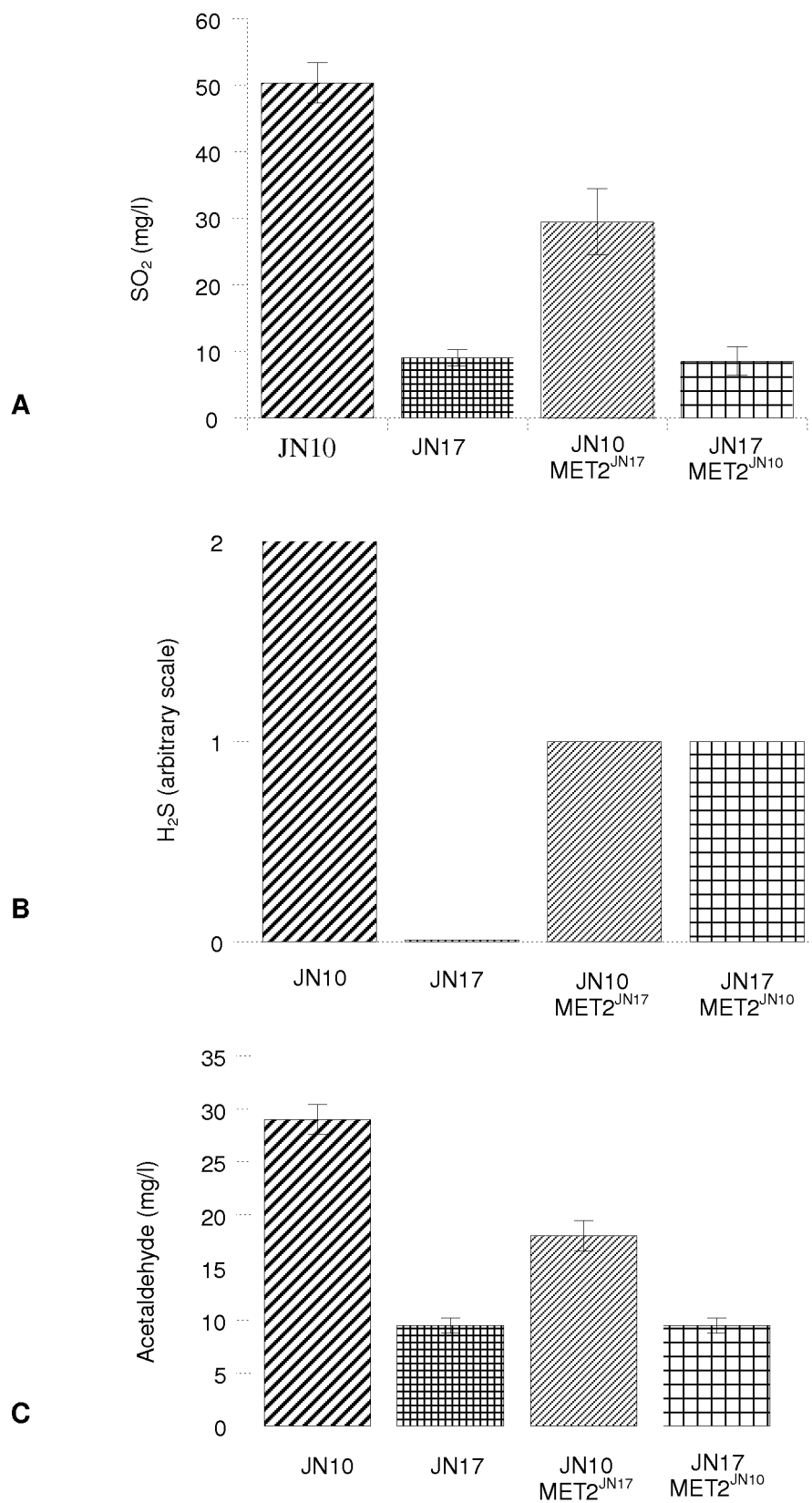
FIG. 1 illustrates the impact of allelic change on the formation of $SO_2$ (A), of $H_2S$ (B) and of acetaldehyde (C) for the JN10 $MET2^{JN17}$ and JN17 $MET2^{JN10}$ strains and the corresponding parent JN10 and JN17 strains.

For example, if the parent strain contains an $SKP2^{(350/357)X}$ allele and a $MET2^{301G}$ allele, it will be possible to introduce herein an $SKP2^{(350/357)I}$ allele. Conversely, if the parent strain contains an $SKP2^{(350/357)I}$ allele and a $MET2^{301X}$ allele, it will be possible to introduce herein a $MET2^{301G}$ allele. If the parent strain contains an $SKP2^{(350/357)X}$ allele and a $MET2^{301X}$ allele, it is possible to introduce herein either an $SKP2^{(350/357)I}$ allele or a $MET2^{301G}$ allele. Preferably, it will be chosen to introduce herein both an $SKP2^{(350/357)I}$ allele and a $MET2^{301G}$ allele.

DETAILED DESCRIPTION

In the context of the disclosure of the present invention, the name "$SKP2^{(350/357)I}$ allele" encompasses: an allele (more specifically known as $SKP2^{350I/357X}$ allele) encoding an Skp2 protein in which the amino acid in position 350 is an isoleucine and the amino acid in position 357 is other than an isoleucine; an allele (more specifically known as $SKP2^{350X/357I}$ allele) encoding an Skp2 protein in which the amino acid in position 350 is other than an isoleucine; an allele (more specifically known as $SKP2^{350I/357I}$ allele) in which the amino acid in position 350 and the amino acid in position 357 are both isoleucines, the latter allele being particularly preferred.

According to one preferred embodiment of the present invention, said parent strain contains an allele of the SKP2 gene, hereinafter known as $SKP2^{350V/357T}$, encoding an Skp2 protein in which the amino acid in position 350 is a valine and/or the amino acid in position 357 is a threonine, and/or an allele of the MET2 gene, hereinafter known as $MET2^{301R}$, encoding a Met2 protein in which the amino acid in position 301 is an arginine.

Advantageously, said yeast strain belongs to the *Saccharomyces cerevisiae* species.

The $SKP2^{(350/357)I}$ allele and/or the $MET2^{301G}$ allele can be introduced into the parent strain by various methods, well known in themselves to those skilled in the art. They can be introduced, for example, by crossing with a strain which has the desired $SKP2^{(350/357)I}$ allele and/or $MET2^{301G}$ allele, and selection from the descendants of this cross, of those to which said allele has been transmitted.

The $SKP2^{(350/357)I}$ allele and/or the $MET2^{301G}$ allele can also be introduced by replacement of the initial allele (respectively $SKP2^{(350/357)X}$ and $MET2^{301X}$) or in addition to said allele, using conventional genetic engineering techniques (cf. for example AMBERG et al., Methods in yeast genetics: a Cold Spring Harbor Laboratory course manual, Cold Spring Harbor Laboratory Press, 2005).

If the method in accordance with the invention is carried out using a haploid parent strain carrying the $SKP2^{(350/357)X}$ allele, the introduction, into said strain, of a copy of the $SKP2^{(350/357)I}$ allele by crossing produces a heterozygous $SKP2^{(350/357)X}/SKP2^{(350/357)I}$ strain, producing an amount of sulfites, hydrogen sulfide and acetaldehyde which is lower than that produced by the parent strain from which it is derived. It is also possible to obtain haploid descendants of this strain which have the $SKP2^{(350/357)I}$ allele and therefore produce low amounts of sulfites, of hydrogen sulfide and of acetaldehyde. By means of the series of backcrosses between descendants having the $SKP2^{(350/357)I}$ allele and the parent strain, it is thus possible to obtain a strain with a genome close to that of the parent strain, having acquired the $SKP2^{(350/357)I}$ allele and producing low amounts of sulfites, of hydrogen sulfide and of acetaldehyde. Likewise, if the method in accordance with the invention is carried out using a parent strain carrying the $MET2^{301X}$ allele, the crossing of said strain with a strain having the $MET2^{301G}$ allele produces a heterozygous $MET2^{301X}/MET2^{301G}$ strain, producing an amount of sulfites, of hydrogen sulfide and of acetaldehyde which is lower than that produced by the parent strain from which it is derived. It is also possible, as in the case of SKP2, to obtain haploid descendants of this strain having the $MET2^{301G}$ allele, and by means of backcrosses with the parent strain, to obtain a strain having the $MET2^{301G}$ allele on the genetic background of the parent strain.

The subject of the present invention is also an isolated polynucleotide encoding the Skp2 protein of sequence SEQ ID NO: 2, which corresponds to the $SKP2^{350I/357I}$ allele.

According to one preferred embodiment of the present invention, this polynucleotide is defined by the sequence SEQ ID NO: 1.

This polynucleotide can be used, in the context of the method in accordance with the invention described above, to introduce the SKP2$^{350I/357I}$ allele into a yeast strain.

A subject of the present invention is also a nucleic acid vector containing a polynucleotide of sequence SEQ ID NO: 1, or a fragment thereof containing at least the region 1045-1075 of SEQ ID NO: 1.

Said vector may be any type of vector usable in yeast, in particular in *Saccharomyces*. Such vectors are well known in themselves. Use may, for example, be made of extrachromosomal replicating vectors, such as the Yep vectors or the Yrp vectors. Use may also be made of integrating vectors such as the Yip vectors.

In the context of an integrating vector, the polynucleotide of sequence SEQ ID NO: 1, or said fragment, is flanked upstream and downstream by sequences of at least 20 bp, preferably of 40 to 60 bp, which are homologues to those flanking the SKP2 gene or the region 1045-1075 of said gene in the strain into which it is desired to introduce the SKP2$^{350I/357I}$ allele.

The DNA fragment containing the sequence SEQ ID NO: 1, or at least the region 1045-1075 of SEQ ID NO: 1, will be optionally combined with a marker gene (gene encoding a protein which confers resistance to an inhibitor or gene which makes it possible to complement a mutation responsible for an auxotrophy of the recipient strain) facilitating the selection of the clones having acquired the fragment by transformation.

A subject of the present invention is also a method for evaluating the capacity of a strain of *Saccharomyces*, preferably of *Saccharomyces cerevisiae*, to produce SO$_2$, hydrogen sulfide and acetaldehyde, characterized in that it comprises:
   genotyping of said strain for the SKP2 gene, and the detection of the presence of an SKP2$^{(350/357)X}$ allele and in particular of the SKP2$^{350V/357T}$ allele, and/or of an SKP2$^{(350/357)I}$ allele, and in particular of the SKP2$^{350I/357I}$ allele; and/or
   the genotyping of said strain for the SKP2 gene, and the detection of the presence of an SKP2$^{(350/357)X}$ allele and in particular of the SKP2$^{350V/357T}$ allele, and/or of an SKP2$^{(350/357)I}$ allele, and in particular of the SKP2$^{350I/357I}$ allele.

A subject of the present invention is also reagents for carrying out the genotyping method in accordance with the invention.

These reagents comprise in particular:
allele-specific oligonucleotide probes for differentiating the SKP2$^{350V/357T}$ allele from an SKP2$^{(350/357)I}$ allele, and in particular from the SKP2$^{350I/357I}$ allele, or for differentiating the MET2$^{301R}$ allele from the MET2$^{301G}$ allele, by hybridizing selectively with one or other of the alleles to be differentiated;
specific primers for differentiating the SKP2$^{350V/357T}$ allele from an SKP2$^{(350/357)I}$ allele, and in particular from the SKP2$^{350I/357I}$ allele, or for differentiating the MET2$^{301R}$ allele from the MET2$^{301G}$ allele, and also kits of primers containing at least one specific primer in accordance with the invention. Generally, these kits of primers comprise a primer specific for each allele to be detected, and a common primer, capable of hybridizing, under the same amplification conditions, with all the alleles of the gene concerned.

Probes in accordance with the invention for differentiating the SKP2$^{350V/357T}$ allele from an SKP2$^{(350/357)I}$ allele, and in particular from the SKP2$^{350I/357I}$ allele, can for example be made up of fragments of 15 to 30 bp of the sequence: CTAGAAAATGTAACGRTAGACACCGAATCGCTAGA-TAYTCCAATGGAATTCTT (SEQ ID NO: 4, where A, T, C, G, R and Y have their usual meaning in the IUPAC code), said fragments containing at least the locus of the G/A polymorphism, or at least the locus of the C/T polymorphism, and where appropriate the 2 polymorphic loci of said sequence, or made up of the sequences complementary thereto.

The probes in which R=G, and also the probes in which Y=C, can hybridize selectively with the SKP2$^{350V/357T}$ allele, while the probes in which R=A and those in which Y=T can hybridize selectively with an SKP2$^{(350/357)I}$ allele, and in particular the SKP2$^{350I/357I}$ allele.

Probes in accordance with the invention for differentiating the MET2$^{301R}$ allele from the MET2$^{301G}$ allele can for example be made up of fragments of 15 to 30 bp of the sequence: ATTTCTGGGCAAAAASGTCAAAGCGTG-GTGT (SEQ ID NO: 3, where A, T, C, G and S have their usual meaning in the IUPAC code), said fragments containing the locus of the C/G polymorphisms of said sequence, or made up of the sequences complementary thereto. The probes in which S=C can hybridize selectively with the MET2$^{301R}$ allele, while the probes in which S=G can hybridize selectively with the MET2$^{301G}$ allele.

Specific primers in accordance with the invention for differentiating SKP2$^{350V}$ from SKP2$^{350I}$ can for example be made up of fragments of 15 to 30 bp of the sequence SEQ ID NO: 4 containing at least the locus of the G/A polymorphism or the sequence complementary thereto. The primers in which R=G can be used for the selective amplification of SKP2$^{350V}$, while the primers in which R=A can be used for the selective amplification of SKP2$^{350I}$.

Specific primers in accordance with the invention for differentiating SKP2$^{357T}$ from SKP2$^{357I}$ can for example be made up of fragments of 15 to 30 bp of the sequence SEQ ID NO: 4 containing at least the locus of the C/T polymorphism, or the sequences complementary thereto.

The primers in which Y=C can be used for the selective amplification of SKP2$^{357T}$ and those in which Y=T can be used for the selective amplification of SKP2$^{357I}$.

According to one preferred embodiment of a kit of primers in accordance with the invention for differentiating the SKP2$^{350V/357T}$ allele from an SKP2$^{(350/357)I}$ allele, it comprises a pair of specific primers for differentiating SKP2$^{350V}$ from SKP2$^{350I}$, and a pair of specific primers for differentiating SKP2$^{357T}$ from SKP2$^{357I}$.

Specific primers in accordance with the invention for differentiating the MET2$^{301R}$ allele from the MET2$^{301G}$ allele can for example be made up of fragments of 15 to 30 bp of the sequence SEQ ID NO: 3 containing at least the locus of the C/G polymorphism in said sequence, or made up of the sequences complementary thereto. The primers in which S=C can be used for the selective amplification of the MET2$^{301R}$ allele, while the primers in which S=G can be used for the selective amplification of the MET2$^{301G}$ allele.

Common primers which can be used in combination with the specific primers for differentiating the MET2$^{301R}$ allele from the MET2$^{301G}$ allele in the kits of primers in accordance with the invention can for example be made up of fragments of 15 to 30 bp of the following sequence: ATGT-TATGCCTGAGGTATGTGTGGTATCTA (SEQ ID NO: 5, where A, T, C and G have their usual meaning in the IUPAC code), or made up of the sequences complementary thereto.

Common primers which can be used in combination with the specific primers for differentiating SKP2$^{350V}$ from SKP2$^{350I}$ and/or with the specific primers for differentiating SKP2$^{357T}$ from SKP2$^{357I}$ in the kits of primers in accordance with the invention can for example be made up of fragments of 15 to 30 bp of the following sequence: AGTCCACTA-CAAAAAGTCATTTATTTTTGC (SEQ ID NO: 6, where A, T, C and G have their usual meaning in the IUPAC code), or made up of the sequences complementary thereto.

The present invention will be understood more clearly from the further description which follows, which refers to nonlimiting examples illustrating the effects of the alleles of the MET2 and SKP2 genes on the production of $SO_2$, of hydrogen sulfide and of acetaldehyde.

THE EXAMPLES

EXAMPLE 1

Effect of the Alleles of the MET2 Gene on the Production of $SO_2$, of Hydrogen Sulfide and of Acetaldehyde The *Saccharomyces cerevisiae* JN10 strain (strong producer of $SO_2$, $H_2S$ and acetaldehyde) has a MET2 gene allele which encodes a Met2 protein in which the amino acid in position 301 is an arginine, whereas the JN17 strain (weak producer of these same compounds) has a MET2 gene allele encoding a Met2 protein in which the amino acid in position 301 is a glycine.

The impact of the replacement of the MET2 allele of JN10 (MET2$^{JN10}$) with that of JN17 (MET2$^{JN17}$), or conversely that of the replacement of the MET2 allele of JN17 with that of JN10, were evaluated.

Firstly, the initial MET2$^{JN10}$ or MET2$^{JN17}$ allele was deleted and replaced with a cassette containing a geneticin-resistance gene (KANMX4), according to the method described by Wach et al. (Yeast, 10, 1793-808, 1994). The transformed cells are selected on the basis of their resistance to the antibiotic, and of their methionine auxotrophy.

The MET2$^{JN17}$ allele amplified from the genomic DNA of the JN17 strain was then introduced, as a replacement for the geneticin-resistance cassette, into the JN10 strain, and vice versa, the MET2$^{JN10}$ allele amplified from the genomic DNA of the JN10 strain was introduced, as a replacement for the geneticin-resistance cassette, into the JN17 strain. The transformed strains are selected on the basis of the restoration of their methionine prototrophy.

The impacts of the allelic change on the formation of $SO_2$, of $H_2S$ and of acetaldehyde were evaluated during alcoholic fermentations under enological conditions.

The results are represented in FIG. 1. A: production of $SO_2$; B: production of $H_2S$; C: production of acetaldehyde.

The replacement of the MET2$^{JN10}$ allele with the MET2$^{JN17}$ allele in the JN10 strain (JN10-MET2$^{JN17}$ strain) leads to a reduction in the concentration of $SO_2$ formed of approximately 40%. Likewise, the production of $H_2S$ is significantly reduced, 1 on a scale ranging from 0 to 2. The acetaldehyde level is also decreased by close to 40%. The reverse allelic replacement (MET2$^{JN10}$ allele on the genetic background of the JN17 strain: JN17-MET2$^{JN10}$ strain) has no impact on the production of $SO_2$, nor on that of acetaldehyde; on the other hand, an increase in the production of $H_2S$ is observed compared with the JN17 parental strain.

EXAMPLE 2

Effect of the Alleles of the SKP2 Gene in the Production of $SO_2$, of Acetaldehyde and of Hydrogen Sulfide The SKP2 gene allele present in the *Saccharomyces cerevisiae* JN10 strain) (SKP2$^{JN10}$) encodes an Skp2 protein in which the amino acid in position 350 is a valine and the amino acid in position 357 is a threonine, whereas the allele present in the JN17 strain (SKP2$^{JN17}$) encodes an Skp2 protein in which the amino acids in positions 350 and 357 are isoleucines.

The impact of the allelic form of the SKP2 gene (SKP2$^{JN10}$ or SKP2$^{JN17}$) was evaluated via the construction of hemizygotes. The allelic replacement was in fact a method that was more difficult to carry out than in the case of the MET2 gene since the inactivation of the SKP2 gene results only in a delay of growth on minimum medium (Yoshida et al., 2011, mentioned above), this being a phenotype which, contrary to the methionine auxotrophy observed in the case of the MET2 gene, is not easily usable as a selectable marker.

Figure 2:
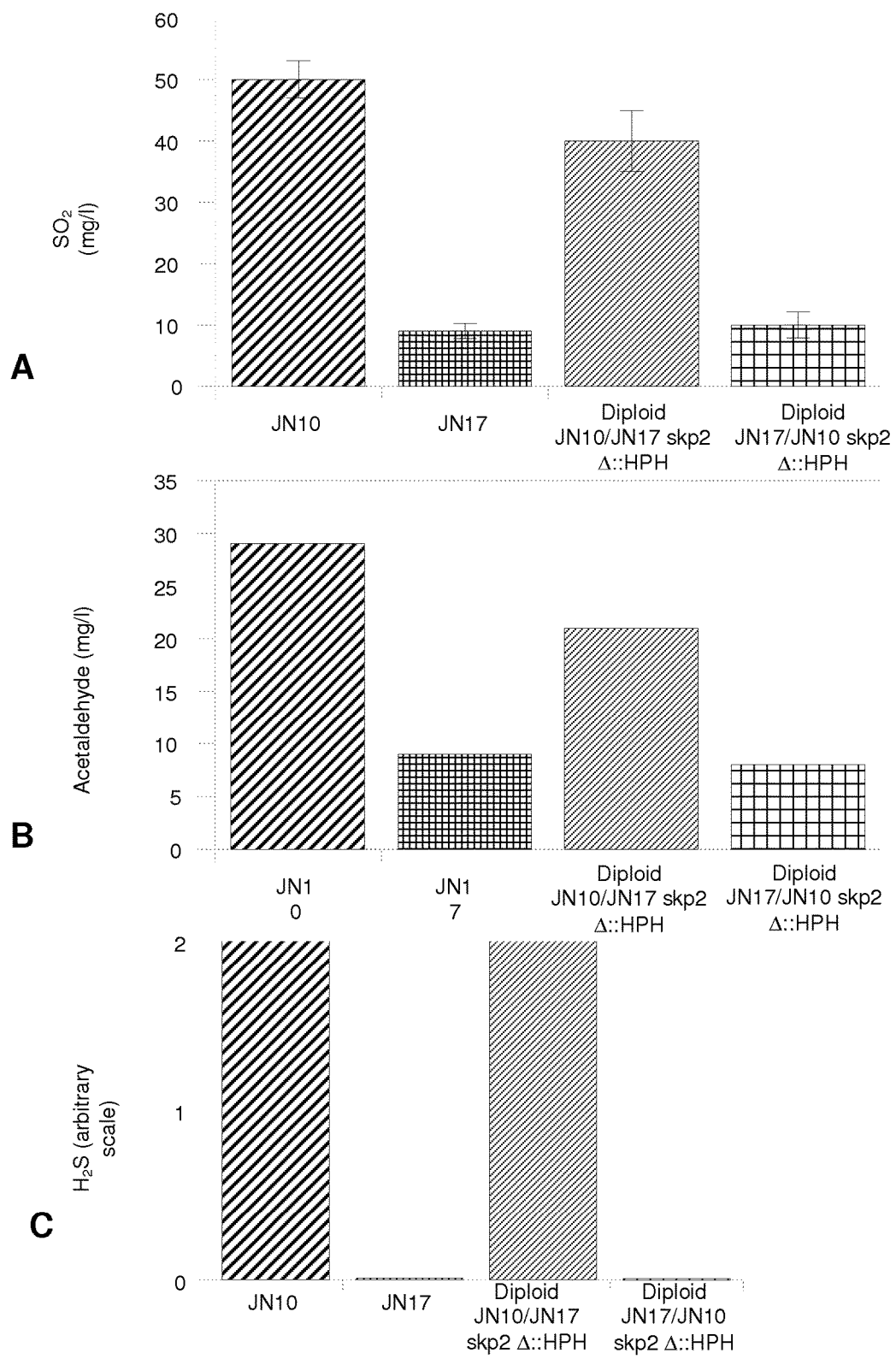
FIG. 2 illustrates the formation of $SO_2$ (A), of $H_2S$ (B) and of acetaldehyde (C) for the diploid strains JN17/JN10skp2☐::HPH and JN10/JN17skp2☐::HPH, which have just one functional allele of SKP2 (respectively the $SKP2^{JN17}$ allele and the $SKP2^{JN10}$ allele). And the corresponding parent JN10 and JN17 strains.

Firstly, the SKP2 gene was inactivated in each of the JN10 and JN17 parental strains, by insertion of the HPH cassette which confers resistance to hygromycin B, so as to obtain respectively the JN10skp2Δ::HPH strains and the JN17skp2Δ::HPH strain. The JN10skp2Δ::HPH strain was then crossed with the JN17 strain, and the JN17skp2Δ::HPH strain was crossed with the JN10 strain, so as to obtain respectively the diploid strains JN17JN10skp2Δ::HPH and JN10/JN17skp2Δ::HPH, which have just one functional allele of SKP2 (respectively the SKP2$^{JN17}$ allele and the SKP2$^{JN10}$ allele). The production of sulfites, of acetaldehyde and of hydrogen sulfide by these strains which are hemizygote for SKP2 was evaluated under enological alcoholic fermentation conditions. The results are shown in FIG. 2. A: production of $SO_2$; B: production of acetaldehyde; C: production of hydrogen sulfide.

It is noted that the production of $SO_2$ is lower in the hemizygote which has the SKP2$^{JN17}$ allele than in that which has the SKP2$^{JN10}$ allele. Likewise, the acetaldehyde content is lower when the SKP2$^{JN17}$ allele is active than when the allele is the one derived from the JN10 strain. Finally, the hydrogen sulfide content is lower when the SKP2$^{JN17}$ allele is active than when the allele is the one derived from the JN10 strain. The SKP2$^{JN17}$ allele therefore results in a reduction in $SO_2$, acetaldehyde and hydrogen sulfide contents.

EXAMPLE 3

Combined Effect of the Alleles of the MET2 and SKP2 Gene of the Production of $SO_2$ and of Hydrogen Sulfide The impact of a combination of the two allelic forms SKP2$^{JN17}$ and MET2$^{JN17}$ was evaluated by means of the construction of virtually isogenic strains having more than 93% of the genome of the JN10 strain, following cycles of backcrosses. The backcrosses consist of a series of successive crosses with the same strain (in this case JN10). The JN17 strain is first of all hybridized with the JN10 strain. The hybrid obtained, which has 50% of the genome of the JN10 strain and 50% of the genome of the JN17 strain and has the following genotype: SKP2$^{JN17}$/SKP2$^{JN10}$ and MET2$^{JN17}$/MET2$^{JN10}$, is induced to sporulate. After sporulation, the haploid spores having the following genotype: SKP2$^{JN17}$ and MET2$^{JN17}$ are selected by allele-specific PCR for these two genes. These spores are then crossed again with the JN10 strain. A new hybrid is obtained, which has 75% of the genome of the JN10 strain and 25% of the genome of the JN17 strain and has the following genotype: SKP2$^{JN17}$/SKP2$^{JN10}$ and MET2$^{JN17}$/MET2$^{JN10}$; this hybrid is in turn induced to sporulate. The asci are dissected and a spore having the following genotype: SKP2$^{JN17}$ and MET2$^{JN17}$ is selected. The cycles of crossing/sporulation/selection of a spore are continued until derivatives having a very high percentage of the genome of the JN10 strain, in this case 93.25%, are obtained.

Figure 3:
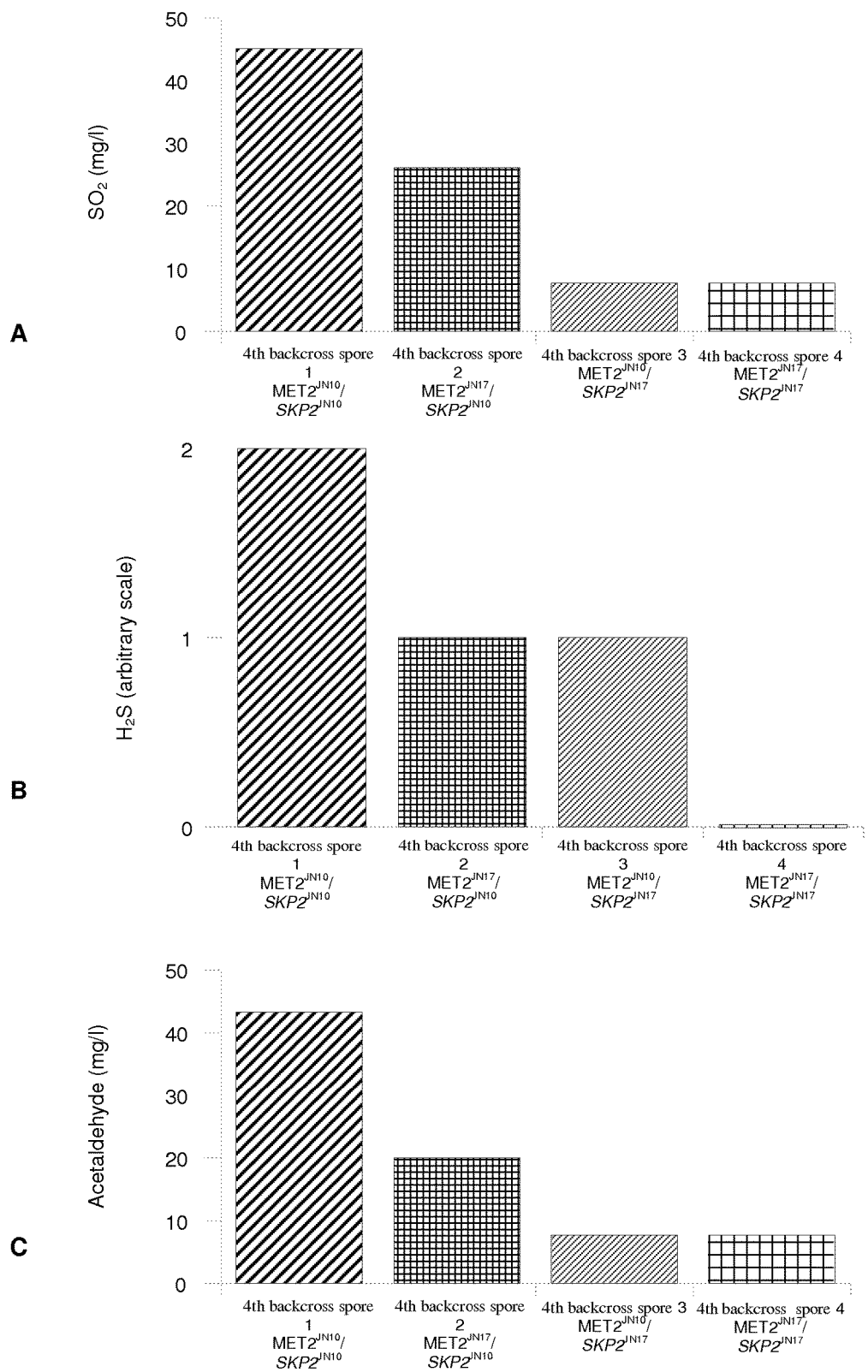
FIG. 3 illustrates the formation of $SO_2$ (A), of $H_2S$ (B) and of acetaldehyde (C) for haploid derivatives (4th backcross spores 1 to 4) having the following allele combinations: $SKP2^{JN17}/MET2^{JN17}$; $SKP2^{JN10}/MET2^{JN17}$; $SKP2^{JN17}/MET2^{JN10}$; $SKP2^{JN10}/MET2^{JN10}$ on virtually identical genetic backgrounds.

By sporulation of the diploid clones obtained during the final cycle, haploid derivatives (4th backcross spores 1 to 4) having the following allele combinations: SKP2$^{JN17}$/MET2$^{JN17}$; SKP2$^{JN10}$/MET2$^{JN17}$; SKP2$^{JN}$17/MET2$^{JN10}$; SKP2$^{JN10}$/MET2$^{JN10}$ on virtually identical genetic backgrounds are obtained. The production of SO$_2$, of H$_2$S and of acetaldehyde of these various derivatives was evaluated under enological alcoholic fermentation conditions. The results are shown in table I below, and by FIG. 3.

TABLE I

| SKP2 allele | MET2 allele | SO$_2$ (mg/l) | H$_2$S | Acetaldehyde (mg/l) |
|---|---|---|---|---|
| JN10 | JN10 | 46 | 2 | 43 |
| JN10 | JN17 | 28 | 1 | 20 |
| JN17 | JN10 | 5 | 1 | 6 |
| JN17 | JN17 | 5 | 0 | 6 |

H$_2$S scale:
0 = production not detected,
1 = medium production,
2 = strong production It is noted that the SO$_2$ production of a derivative which has the two alleles SKP2$^{JN10}$/MET2$^{JN10}$ is identical to that of the initial JN10 strain, whereas a derivative which has a combination of alleles of SKP2$^{JN10}$/MET2$^{JN17}$ type produces intermediate amounts of SO$_2$. Moreover, derivatives which have either the SKP2$^{JN17}$/MET2$^{JN10}$ allele combination or the two alleles of the JN17 strain, SKP2$^{JN17}$/MET2$^{JN17}$, both produce very low amounts of SO$_2$ which are identical to those of the initial JN17 strain.

The effect of the various allele combinations on the production of acetaldehyde is identical to that observed on the production of SO$_2$.

Furthermore, the derivatives which have the two alleles of the JN10 strain produce high amounts of H$_2$S, identical to the JN10 parental strain, while the derivatives which have one of the two alleles of the JN17 strain, and therefore have the following genotypes: SKP2$^{JN17}$/MET2$^{JN10}$ or SKP2$^{JN10}$/MET2$^{JN17}$, produce H$_2$S in intermediate amounts and only the derivative which has the two alleles SKP2$^{JN17}$/MET2$^{JN17}$ does not produce detectable H$_2$S, in the same way as the JN17 parental strain.

The invention claimed is:

1. A method for obtaining a yeast strain of the genus *Saccharomyces* producing an amount of SO$_2$, of hydrogen sulfide and of acetaldehyde which is lower than that produced by the parent strain from which it is derived, said method being characterized in that it comprises:

the selection of a parent strain containing an allele of the SKP2 gene, hereinafter known as SKP2$^{(350/357X)}$, encoding a Skp2 protein in which the amino acid in position 350 and the amino acid in position 357 are other than isoleucines, and/or an allele of the MET2 gene, hereinafter known as MET2$^{301X}$, encoding a Met2 protein in which the amino acid in position 301 is other than a glycine; and the introduction, into said parent strain, of an allele of the SKP2 gene, hereinafter known as SKP2$^{(350/357)I}$, encoding a Skp2 protein in which the amino acid in position 350 and the amino acid in position 357 are isoleucines, and/or of an allele of the MET2 gene, hereinafter known as MET2$^{301G}$, encoding a Met2 protein in which the amino acid in position 301 is a glycine, wherein said yeast strain belongs to the *Saccharomyces cervisiae* species.

2. The method as claimed in claim 1, characterized in that said parent strain contains an allele of the SKP2 gene, hereinafter known as SKP2$^{350V/357T}$, encoding a Skp2 protein in which the amino acid in position 350 is a valine and/or the amino acid in position 357 is a threonine, and/or an allele of the MET2 gene, hereinafter known as MET2$^{301R}$, encoding a Met2 protein in which the amino acid in position 301 is an arginine.

3. The method as claimed in claim 1, characterized in that said parent strain contains an allele of the SKP2 gene, hereinafter known as SKP2$^{350V/357T}$, encoding a Skp2 protein in which the amino acid in position 350 is a valine and the amino acid in position 357 is a threonine.

4. The method as claimed in claim 1, characterized in that said parent strain contains an allele of the SKP2 gene, hereinafter known as SKP2$^{350V/357T}$, encoding a Skp2 protein in which the amino acid in position 350 is a valine and the amino acid in position 357 is a threonine and an allele of the MET2 gene, hereinafter known as MET2$^{301R}$, encoding a Met2 protein in which the amino acid in position 301 is an arginine.

* * * * *

SEQUENCE LISTING

<160> NUMBER OF SEQ ID NOS: 6

<210> SEQ ID NO 1
<211> LENGTH: 2292
<212> TYPE: DNA
<213> ORGANISM: Saccharomyces cerevisiae
<220> FEATURE:
<221> NAME/KEY: CDS
<222> LOCATION: (1)..(2292)

<400> SEQUENCE: 1

```
atg aaa cgg ttg caa ttg ttt ggt aga tca aaa tat ttc tcg ctg gtc        48
Met Lys Arg Leu Gln Leu Phe Gly Arg Ser Lys Tyr Phe Ser Leu Val
1               5                   10                  15 tcc agt gct gcg aag gag gaa gaa gag gaa gag ggc tgt gct gat             96
Ser Ser Ala Ala Lys Glu Glu Glu Glu Glu Glu Gly Cys Ala Asp
            20                  25                  30 gcc aaa agc ctt cta cat agt acg agc cat gat atc aaa tcg aga tca       144
Ala Lys Ser Leu Leu His Ser Thr Ser His Asp Ile Lys Ser Arg Ser
        35                  40                  45 cta cgc ttc aac gat aaa tcg tcc ctc atg tgt ttg cca aca aaa gtt       192
Leu Arg Phe Asn Asp Lys Ser Ser Leu Met Cys Leu Pro Thr Lys Val
    50                  55                  60 cta ctg tta ata ctg cga act ttg gac ttc aat aca tta gta aca cta       240
Leu Leu Leu Ile Leu Arg Thr Leu Asp Phe Asn Thr Leu Val Thr Leu
65                  70                  75                  80 tgc caa gtc aat tcg agg ttc tac aat ttg att acg aat gag ttc ctt       288
Cys Gln Val Asn Ser Arg Phe Tyr Asn Leu Ile Thr Asn Glu Phe Leu
                85                  90                  95 ttc caa aac gtt att ttg gac tca aaa ctt tcg ttg tta aag ttc aat       336
Phe Gln Asn Val Ile Leu Asp Ser Lys Leu Ser Leu Leu Lys Phe Asn
            100                 105                 110
```

```
gct ttg ata cac tcc gag ttc cac acg tcg aac att gtc aca cac agc      384
Ala Leu Ile His Ser Glu Phe His Thr Ser Asn Ile Val Thr His Ser
        115                 120                 125 ggt gat tgt agc aca caa tct aga tca caa aat gca agg ttc ctc gta      432
Gly Asp Cys Ser Thr Gln Ser Arg Ser Gln Asn Ala Arg Phe Leu Val
130                 135                 140 aga tcc atc gaa ttc aaa aat cct cag tcc caa gac tcg ttg tta aaa      480
Arg Ser Ile Glu Phe Lys Asn Pro Gln Ser Gln Asp Ser Leu Leu Lys
145                 150                 155                 160 tac agt aag ttc tat aat aag agt ggc caa gat tct att att gct gga      528
Tyr Ser Lys Phe Tyr Asn Lys Ser Gly Gln Asp Ser Ile Ile Ala Gly
                165                 170                 175 tct tat aaa ctc gat tcg tat gat aaa gac gta aaa aaa ctg aat aac      576
Ser Tyr Lys Leu Asp Ser Tyr Asp Lys Asp Val Lys Lys Leu Asn Asn
            180                 185                 190 atc aga cta aac gat gag act ccc atc ata act tca gaa cga atc aaa      624
Ile Arg Leu Asn Asp Glu Thr Pro Ile Ile Thr Ser Glu Arg Ile Lys
        195                 200                 205 ctg ctt gat aaa ttg gaa agc aac tac ttc cat tat act tat att gag      672
Leu Leu Asp Lys Leu Glu Ser Asn Tyr Phe His Tyr Thr Tyr Ile Glu
    210                 215                 220 cta atg ctt gat att ata gac tat cta ccg aac ctg acc aga gtg att      720
Leu Met Leu Asp Ile Ile Asp Tyr Leu Pro Asn Leu Thr Arg Val Ile
225                 230                 235                 240 ctg agt gat gtg gaa ccg aat ttt aaa att cct tta tgg tac tct gta      768
Leu Ser Asp Val Glu Pro Asn Phe Lys Ile Pro Leu Trp Tyr Ser Val
                245                 250                 255 ttc aac gat gga tct aga gat ttt ttc aag aaa ata atc aag ggc cag      816
Phe Asn Asp Gly Ser Arg Asp Phe Phe Lys Lys Ile Ile Lys Gly Gln
            260                 265                 270 caa tcc atc aca aac gaa gat ttg agg act ttc caa cta tcc aaa aaa      864
Gln Ser Ile Thr Asn Glu Asp Leu Arg Thr Phe Gln Leu Ser Lys Lys
        275                 280                 285 ttt gtc aaa gaa tac gaa tcc aag tat tat tct ctg cca agg ttg aaa      912
Phe Val Lys Glu Tyr Glu Ser Lys Tyr Tyr Ser Leu Pro Arg Leu Lys
    290                 295                 300 ata ctg gaa atc aaa gct aat aat aaa aga caa aga acc ttt aat cgt      960
Ile Leu Glu Ile Lys Ala Asn Asn Lys Arg Gln Arg Thr Phe Asn Arg
305                 310                 315                 320 caa cgc cat cac caa aag ctc gta cta aga ccg agt tta ttc tgc tgt     1008
Gln Arg His His Gln Lys Leu Val Leu Arg Pro Ser Leu Phe Cys Cys
                325                 330                 335 ttc ggc ata att aat gaa ctt aaa cta gaa aat gta acg ata gac acc     1056
Phe Gly Ile Ile Asn Glu Leu Lys Leu Glu Asn Val Thr Ile Asp Thr
            340                 345                 350 gaa tcg cta gat att cca atg gaa ttc tta cca cta ttt cta aag aac     1104
Glu Ser Leu Asp Ile Pro Met Glu Phe Leu Pro Leu Phe Leu Lys Asn
        355                 360                 365 gaa gat aat gaa ctg tac agt tta cag tct cct atc act gca ctt act     1152
Glu Asp Asn Glu Leu Tyr Ser Leu Gln Ser Pro Ile Thr Ala Leu Thr
    370                 375                 380 tta gat tca tgt gat gta gtt cct gga aat gga ata tta cgt ttg ttt     1200
Leu Asp Ser Cys Asp Val Val Pro Gly Asn Gly Ile Leu Arg Leu Phe
385                 390                 395                 400 cac tct tac ttt aaa atg gtc aaa cat cta tcc tta ctg aag att aac     1248
His Ser Tyr Phe Lys Met Val Lys His Leu Ser Leu Leu Lys Ile Asn
                405                 410                 415 agt aaa ttc gac tta ttg tta tgc agt tgt ttc cca tcg tta tcc aat     1296
Ser Lys Phe Asp Leu Leu Leu Cys Ser Cys Phe Pro Ser Leu Ser Asn
```

-continued

|     |     |     |     |     |     |     |     |     |     |     |     |     |     |     |     |      |
|---|---|---|---|---|---|---|---|---|---|---|---|---|---|---|---|---|
|     |     |     | 420 |     |     |     | 425 |     |     |     | 430 |     |     |     |     |      |
| cta | aca | att | gat | tgt | aat | agc | aaa | tgt | ttc | act | aac | gaa | cag | gta | gtc | 1344 |
| Leu | Thr | Ile | Asp | Cys | Asn | Ser | Lys | Cys | Phe | Thr | Asn | Glu | Gln | Val | Val |      |
|     |     | 435 |     |     |     |     | 440 |     |     |     |     | 445 |     |     |     |      |
| ggc | gaa | tca | tat | tat | ttc | caa | cag | cga | agt | ttg | gat | aca | gaa | gat | gat | 1392 |
| Gly | Glu | Ser | Tyr | Tyr | Phe | Gln | Gln | Arg | Ser | Leu | Asp | Thr | Glu | Asp | Asp |      |
|     | 450 |     |     |     |     | 455 |     |     |     |     | 460 |     |     |     |     |      |
| ttt | gat | gac | tgc | aat | tcc | atg | aca | gaa | aca | tta | ttt | gaa | gcg | cca | tca | 1440 |
| Phe | Asp | Asp | Cys | Asn | Ser | Met | Thr | Glu | Thr | Leu | Phe | Glu | Ala | Pro | Ser |      |
| 465 |     |     |     |     | 470 |     |     |     |     | 475 |     |     |     |     | 480 |      |
| gat | tcg | aag | ata | att | act | cct | ccg | ccg | aca | tct | tca | gtt | gta | ttg | tcc | 1488 |
| Asp | Ser | Lys | Ile | Ile | Thr | Pro | Pro | Pro | Thr | Ser | Ser | Val | Val | Leu | Ser |      |
|     |     |     |     | 485 |     |     |     |     | 490 |     |     |     |     | 495 |     |      |
| tta | aat | ctg | aac | tat | att | tct | aga | act | aca | gga | aat | gat | gtt | tca | aat | 1536 |
| Leu | Asn | Leu | Asn | Tyr | Ile | Ser | Arg | Thr | Thr | Gly | Asn | Asp | Val | Ser | Asn |      |
|     |     | 500 |     |     |     |     | 505 |     |     |     |     | 510 |     |     |     |      |
| aac | cca | tca | cca | gac | aat | aac | aaa | aag | ccc | gcc | atg | tta | act | gcg | gca | 1584 |
| Asn | Pro | Ser | Pro | Asp | Asn | Asn | Lys | Lys | Pro | Ala | Met | Leu | Thr | Ala | Ala |      |
|     | 515 |     |     |     |     | 520 |     |     |     |     | 525 |     |     |     |     |      |
| cag | cta | caa | aat | ttt | caa | cga | caa | aga | atc | cct | gaa | ttt | cat | tct | ttc | 1632 |
| Gln | Leu | Gln | Asn | Phe | Gln | Arg | Gln | Arg | Ile | Pro | Glu | Phe | His | Ser | Phe |      |
| 530 |     |     |     |     | 535 |     |     |     |     | 540 |     |     |     |     |     |      |
| tac | cat | tat | tac | cgc | tta | ctt | tgg | gag | aga | ctt | cca | agt | aaa | aat | att | 1680 |
| Tyr | His | Tyr | Tyr | Arg | Leu | Leu | Trp | Glu | Arg | Leu | Pro | Ser | Lys | Asn | Ile |      |
| 545 |     |     |     |     | 550 |     |     |     |     | 555 |     |     |     |     | 560 |      |
| tct | att | aac | gta | atc | aat | atc | ccc | ttt | acc | aat | gtg | tat | cct | tta | tcc | 1728 |
| Ser | Ile | Asn | Val | Ile | Asn | Ile | Pro | Phe | Thr | Asn | Val | Tyr | Pro | Leu | Ser |      |
|     |     |     |     | 565 |     |     |     |     | 570 |     |     |     |     | 575 |     |      |
| cct | cta | tcg | ttt | tgg | gaa | cat | cta | gca | aga | aca | att | act | agt | gtt | gat | 1776 |
| Pro | Leu | Ser | Phe | Trp | Glu | His | Leu | Ala | Arg | Thr | Ile | Thr | Ser | Val | Asp |      |
|     |     |     | 580 |     |     |     |     | 585 |     |     |     |     | 590 |     |     |      |
| gag | aca | gat | gag | gat | gtt | ggc | gac | gag | aac | gat | caa | gaa | aca | tta | atc | 1824 |
| Glu | Thr | Asp | Glu | Asp | Val | Gly | Asp | Glu | Asn | Asp | Gln | Glu | Thr | Leu | Ile |      |
|     |     | 595 |     |     |     |     | 600 |     |     |     |     | 605 |     |     |     |      |
| ggt | tac | gaa | aat | aat | tcc | ata | aga | gat | aac | ata | cca | aat | gct | aat | gca | 1872 |
| Gly | Tyr | Glu | Asn | Asn | Ser | Ile | Arg | Asp | Asn | Ile | Pro | Asn | Ala | Asn | Ala |      |
|     | 610 |     |     |     |     | 615 |     |     |     |     | 620 |     |     |     |     |      |
| gtt | cca | aat | tta | agt | aca | gta | atg | agc | cct | gaa | tca | gac | att | cac | cac | 1920 |
| Val | Pro | Asn | Leu | Ser | Thr | Val | Met | Ser | Pro | Glu | Ser | Asp | Ile | His | His |      |
| 625 |     |     |     |     | 630 |     |     |     |     | 635 |     |     |     |     | 640 |      |
| act | tac | tat | tgg | aac | aac | tct | gta | agg | cgt | tgc | cta | aga | gat | agt | tta | 1968 |
| Thr | Tyr | Tyr | Trp | Asn | Asn | Ser | Val | Arg | Arg | Cys | Leu | Arg | Asp | Ser | Leu |      |
|     |     |     |     | 645 |     |     |     |     | 650 |     |     |     |     | 655 |     |      |
| atc | aaa | ttg | aag | aac | cga | acc | atc | gaa | tat | aga | gat | tta | gat | gtg | gag | 2016 |
| Ile | Lys | Leu | Lys | Asn | Arg | Thr | Ile | Glu | Tyr | Arg | Asp | Leu | Asp | Val | Glu |      |
|     |     |     | 660 |     |     |     |     | 665 |     |     |     |     | 670 |     |     |      |
| gag | ttc | tta | caa | aat | gtg | aca | ttg | gaa | aat | ttt | ttc | aat | gat | ttc | caa | 2064 |
| Glu | Phe | Leu | Gln | Asn | Val | Thr | Leu | Glu | Asn | Phe | Phe | Asn | Asp | Phe | Gln |      |
|     |     | 675 |     |     |     |     | 680 |     |     |     |     | 685 |     |     |     |      |
| gat | cca | gag | aat | ttt | aaa | gat | att | cca | aat | att | aac | ctc | tgg | tgt | ttc | 2112 |
| Asp | Pro | Glu | Asn | Phe | Lys | Asp | Ile | Pro | Asn | Ile | Asn | Leu | Trp | Cys | Phe |      |
|     | 690 |     |     |     |     | 695 |     |     |     |     | 700 |     |     |     |     |      |
| ctg | aga | aat | ttg | tca | aaa | ttc | aaa | gct | gtc | aaa | ata | aga | atg | ctg | aga | 2160 |
| Leu | Arg | Asn | Leu | Ser | Lys | Phe | Lys | Ala | Val | Lys | Ile | Arg | Met | Leu | Arg |      |
| 705 |     |     |     |     | 710 |     |     |     |     | 715 |     |     |     |     | 720 |      |
| cat | ttt | tca | tta | tgt | aca | cct | aga | acc | aga | tac | gac | tgg | gaa | cta | tta | 2208 |
| His | Phe | Ser | Leu | Cys | Thr | Pro | Arg | Thr | Arg | Tyr | Asp | Trp | Glu | Leu | Leu |      |
|     |     |     |     | 725 |     |     |     |     | 730 |     |     |     |     | 735 |     |      |
| ttg | aag | ccc | gta | ctg | cgt | gta | aat | gtt | ccc | att | gaa | gtc | aga | gat | aag | 2256 |

-continued

```
Leu Lys Pro Val Leu Arg Val Asn Val Pro Ile Glu Val Arg Asp Lys
                740                 745                 750 gac gga ttc gtt ctt tat tct tac ggg caa aaa taa                    2292
Asp Gly Phe Val Leu Tyr Ser Tyr Gly Gln Lys
        755                 760
```

<210> SEQ ID NO 2
<211> LENGTH: 763
<212> TYPE: PRT
<213> ORGANISM: Saccharomyces cerevisiae

<400> SEQUENCE: 2

```
Met Lys Arg Leu Gln Leu Phe Gly Arg Ser Lys Tyr Phe Ser Leu Val
 1               5                  10                  15

Ser Ser Ala Ala Lys Glu Glu Glu Glu Glu Glu Gly Cys Ala Asp
            20                  25                  30

Ala Lys Ser Leu Leu His Ser Thr Ser His Asp Ile Lys Ser Arg Ser
        35                  40                  45

Leu Arg Phe Asn Asp Lys Ser Ser Leu Met Cys Leu Pro Thr Lys Val
    50                  55                  60

Leu Leu Ile Leu Arg Thr Leu Asp Phe Asn Thr Leu Val Thr Leu
65                  70                  75                  80

Cys Gln Val Asn Ser Arg Phe Tyr Asn Leu Ile Thr Asn Glu Phe Leu
                85                  90                  95

Phe Gln Asn Val Ile Leu Asp Ser Lys Leu Ser Leu Lys Phe Asn
            100                 105                 110

Ala Leu Ile His Ser Glu Phe His Thr Ser Asn Ile Val Thr His Ser
        115                 120                 125

Gly Asp Cys Ser Thr Gln Ser Arg Ser Gln Asn Ala Arg Phe Leu Val
    130                 135                 140

Arg Ser Ile Glu Phe Lys Asn Pro Gln Ser Gln Asp Ser Leu Leu Lys
145                 150                 155                 160

Tyr Ser Lys Phe Tyr Asn Lys Ser Gly Gln Asp Ser Ile Ile Ala Gly
                165                 170                 175

Ser Tyr Lys Leu Asp Ser Tyr Asp Lys Asp Val Lys Lys Leu Asn Asn
            180                 185                 190

Ile Arg Leu Asn Asp Glu Thr Pro Ile Ile Thr Ser Glu Arg Ile Lys
        195                 200                 205

Leu Leu Asp Lys Leu Glu Ser Asn Tyr Phe His Tyr Thr Tyr Ile Glu
    210                 215                 220

Leu Met Leu Asp Ile Ile Asp Tyr Leu Pro Asn Leu Thr Arg Val Ile
225                 230                 235                 240

Leu Ser Asp Val Glu Pro Asn Phe Lys Ile Pro Leu Trp Tyr Ser Val
                245                 250                 255

Phe Asn Asp Gly Ser Arg Asp Phe Lys Lys Ile Lys Gly Gln
            260                 265                 270

Gln Ser Ile Thr Asn Glu Asp Leu Arg Thr Phe Gln Leu Ser Lys Lys
        275                 280                 285

Phe Val Lys Glu Tyr Glu Ser Lys Tyr Tyr Ser Leu Pro Arg Leu Lys
    290                 295                 300

Ile Leu Glu Ile Lys Ala Asn Asn Lys Arg Gln Arg Thr Phe Asn Arg
305                 310                 315                 320

Gln Arg His His Gln Lys Leu Val Leu Arg Pro Ser Leu Phe Cys Cys
                325                 330                 335

Phe Gly Ile Ile Asn Glu Leu Lys Leu Glu Asn Val Thr Ile Asp Thr
```

```
                340             345             350
Glu Ser Leu Asp Ile Pro Met Glu Phe Leu Pro Leu Phe Leu Lys Asn
            355                 360                 365
Glu Asp Asn Glu Leu Tyr Ser Leu Gln Ser Pro Ile Thr Ala Leu Thr
        370                 375                 380
Leu Asp Ser Cys Asp Val Val Pro Gly Asn Gly Ile Leu Arg Leu Phe
385                 390                 395                 400
His Ser Tyr Phe Lys Met Val Lys His Leu Ser Leu Leu Lys Ile Asn
                405                 410                 415
Ser Lys Phe Asp Leu Leu Leu Cys Ser Cys Phe Pro Ser Leu Ser Asn
            420                 425                 430
Leu Thr Ile Asp Cys Asn Ser Lys Cys Phe Thr Asn Glu Gln Val Val
        435                 440                 445
Gly Glu Ser Tyr Tyr Phe Gln Gln Arg Ser Leu Asp Thr Glu Asp Asp
    450                 455                 460
Phe Asp Asp Cys Asn Ser Met Thr Glu Thr Leu Phe Glu Ala Pro Ser
465                 470                 475                 480
Asp Ser Lys Ile Ile Thr Pro Pro Thr Ser Ser Val Val Leu Ser
                485                 490                 495
Leu Asn Leu Asn Tyr Ile Ser Arg Thr Thr Gly Asn Asp Val Ser Asn
            500                 505                 510
Asn Pro Ser Pro Asp Asn Asn Lys Lys Pro Ala Met Leu Thr Ala Ala
        515                 520                 525
Gln Leu Gln Asn Phe Gln Arg Gln Ile Pro Glu Phe His Ser Phe
    530                 535                 540
Tyr His Tyr Arg Leu Leu Trp Glu Arg Leu Pro Ser Lys Asn Ile
545                 550                 555                 560
Ser Ile Asn Val Ile Asn Ile Pro Phe Thr Asn Val Tyr Pro Leu Ser
                565                 570                 575
Pro Leu Ser Phe Trp Glu His Leu Ala Arg Thr Ile Thr Ser Val Asp
            580                 585                 590
Glu Thr Asp Glu Asp Val Gly Asp Glu Asn Asp Gln Glu Thr Leu Ile
        595                 600                 605
Gly Tyr Glu Asn Asn Ser Ile Arg Asp Asn Ile Pro Asn Ala Asn Ala
    610                 615                 620
Val Pro Asn Leu Ser Thr Val Met Ser Pro Glu Ser Asp Ile His His
625                 630                 635                 640
Thr Tyr Tyr Trp Asn Asn Ser Val Arg Arg Cys Leu Arg Asp Ser Leu
                645                 650                 655
Ile Lys Leu Lys Asn Arg Thr Ile Glu Tyr Arg Asp Leu Asp Val Glu
            660                 665                 670
Glu Phe Leu Gln Asn Val Thr Leu Glu Asn Phe Phe Asn Asp Phe Gln
        675                 680                 685
Asp Pro Glu Asn Phe Lys Asp Ile Pro Asn Ile Asn Leu Trp Cys Phe
    690                 695                 700
Leu Arg Asn Leu Ser Lys Phe Lys Ala Val Lys Ile Arg Met Leu Arg
705                 710                 715                 720
His Phe Ser Leu Cys Thr Pro Arg Thr Arg Tyr Asp Trp Glu Leu Leu
                725                 730                 735
Leu Lys Pro Val Leu Arg Val Asn Val Pro Ile Glu Val Arg Asp Lys
            740                 745                 750
Asp Gly Phe Val Leu Tyr Ser Tyr Gly Gln Lys
            755                 760
```

```
<210> SEQ ID NO 3
<211> LENGTH: 31
<212> TYPE: DNA
<213> ORGANISM: Saccharomyces cerevisiae

<400> SEQUENCE: 3
atttctgggc aaaaasgtca aagcgtggtg t                              31

<210> SEQ ID NO 4
<211> LENGTH: 53
<212> TYPE: DNA
<213> ORGANISM: Saccharomyces cerevisiae

<400> SEQUENCE: 4
ctagaaaatg taacgrtaga caccgaatcg ctagataytc caatggaatt ctt      53

<210> SEQ ID NO 5
<211> LENGTH: 30
<212> TYPE: DNA
<213> ORGANISM: Saccharomyces cerevisiae

<400> SEQUENCE: 5
atgttatgcc tgaggtatgt gtggtatcta                                30

<210> SEQ ID NO 6
<211> LENGTH: 30
<212> TYPE: DNA
<213> ORGANISM: Saccharomyces cerevisiae

<400> SEQUENCE: 6
agtccactac aaaaagtcat ttatttttgc                                30
```